United States Patent [19]
Zlotnik et al.

[11] Patent Number: 6,105,916
[45] Date of Patent: Aug. 22, 2000

[54] FRAME ASSEMBLY FOR DEODORANT CABINET

[75] Inventors: Arnold H. Zlotnik, Pgh.; John A. Austin, Bakerstown; Milton Zlotnik, West Homestead, all of Pa.

[73] Assignee: Pestco, Inc., Pittsburgh, Pa.

[21] Appl. No.: 08/370,540

[22] Filed: Jan. 9, 1995

[51] Int. Cl.[7] .............................. A47K 1/08; A61L 9/04; A47B 47/00
[52] U.S. Cl. .................. 248/311.2; 239/57; 312/263
[58] Field of Search .................. 248/311.2; 403/231, 403/382, 903; 312/257.1, 263; 239/55, 57

[56] References Cited

U.S. PATENT DOCUMENTS

| | | | |
|---|---|---|---|
| 3,313,587 | 4/1967 | Mongesku et al. | 312/263 X |
| 4,277,122 | 7/1981 | Bargiel | 312/263 X |
| 4,830,791 | 5/1989 | Muderlak et al. | 239/57 X |
| 4,931,258 | 6/1990 | Zlotnik et al. | 239/55 X |
| 5,324,490 | 6/1994 | Van Vlahakis et al. | 239/55 X |
| 5,360,263 | 11/1994 | Nakano et al. | 312/263 X |
| 5,372,415 | 12/1994 | Tisbo et al. | 312/263 X |

*Primary Examiner*—Ramon O. Ramirez
*Assistant Examiner*—Anita M. King
*Attorney, Agent, or Firm*—Clifford A. Poff

[57] ABSTRACT

A frame for a cabinet for a deodorant particularly for commodes and urinals in public facilities. The frame is composed of separate back plate, top member and bottom member composed of a resilient plastic. The top member and bottom member are snap-locked to the back plate and secured further by projections from the top and bottom members in slots in the back plate. The bottom member is a liquid-tight tray capable of processing deodorants in bottles through wicks or can with wicks, absorbent surcotas and wafers. There is a bottle holder snap-locked to the underside of the top member. A battery-blower assembly is snap-locked to the back plate. The battery poles are joined to the wires from the blower-motor by a clip. The tube which drips deodorant into a commode or urinal is secured to the outlet from the tray by ribs and bulkhead fittings are dispensed with.

14 Claims, 9 Drawing Sheets

FRAME ASSEMBLY FOR DEODORANT CABINET

REFERENCE TO RELATED PATENT

U.S. Pat. No. 4,931,258, Zlotnik et al. (herein Zlotnik), is incorporated in this application by reference.

BACKGROUND OF THE INVENTION

This invention relates to deodorizers such as are used to deodorize commodes and urinals, particularly in the toilets of institutions and places frequented by the public, although it may also be used in homes. Particularly, this invention relates to cabinets for such deodorizers. More specifically, this invention concerns itself with the frame on which the housing of the cabinet is mounted and facilities carried by the frame.

Typical of the teachings of the prior art relating to this invention is Zlotnik. Zlotnik discloses a deodorant cabinet which has given satisfactory service. But Zlotnik has deficiencies which it is desirable to overcome and it is an object of this invention to provide a deodorant cabinet which does not suffer from the deficiencies of Zlotnik.

The frame 3 (FIG. 5) of Zlotnik includes a back plate 13, a top plate 14 and a bottom plate 15. The frame, including its back plate, top plate and bottom plate, is molded as an integral unit, with possible stress-related cracking in the corners due to vandalism once a deodorizer including the frame is in use. Following the completion of the molding operation, it is necessary to remove the frame as a unit. This presents a serious problem since the top and bottom plates, being at right angles to the back plate, cannot be removed with the back plate by raising the frame parallel to the back plate. It is necessary that the mold have retractors at the top and bottom plates which are displaced during removal from the mold at about 45° to the horizontal to free the top and bottom plates for removal. The removal of the frame from the mold is thus a time-consuming and costly process, adding tremendously to the final cost of the finished product. An additional item of cost is that the removal of the frame sometimes distorts the joints between the back plate and the top or bottom plates and recasting is required. The molding and removal process also requires joints of small thickness so that the frame is not as highly stress-resistant at the joints as is desirable.

It is an object of this invention to overcome the above-described deficiencies of the prior-art frame and to provide a relatively low-cost method of producing a molded frame for a deodorant cabinet in whose practice the parts of the frame shall be readily removable from the mold without resulting distortion at the joints between its parts. It is also an object of this invention to provide a frame which shall lend itself to relatively low-cost manufacture and which shall be highly stress resistant at the joints between its parts. The achievements of the objects of this invention have other ancillary advantages which will be described herein.

SUMMARY OF THE INVENTION

In accordance with this invention, there is provided a method or process for producing an integrated frame assembly for a deodorant cabinet in which the parts of the casing are molded separately and are joined mechanically after they are molded. An important feature of this invention is that the material from which the parts are molded is a resilient plastic. The resilience of the plastic is effective in snap-locking the parts into a rigid structure at their joints. typically, the plastic is composed of 80% polypropylene and 20% fiberglass and is currently available from any plastic supply house, for example, Polymer Land, P.O. Box 641071, Pittsburgh, Pa. 15264. Other resilient plastics or resilient materials of other compositions can also be used. For example, the plastic consisting predominantly of acrylic butylene and styrene could be used.

The frame, according to this invention, includes a back plate corresponding to the back plate of Zlotnik, a top member corresponding to the top plate of Zlotnik and a bottom member corresponding to the bottom plate of Zlotnik. In the practice of this invention, the back plate, the top member and the bottom member and blades for a fan are molded in a single mold. The top member is a plate having near its inner end locking tabs which, when this member is engaged with the back plate, ride on a ramp near the top of the back plate and are compressed. When the top member reaches the back plate, the tab leaves the ramp and relaxes snapping into rigid locking position.

The bottom member is a liquid-tight tray which carries near the inner end of its bottom locking tabs similar to those on the top member. When the bottom member is moved into engagement with the back plate, the locking members ride on a ramp and on leaving the ramp, snap into locking engagement with the back plate producing a rigid joint.

The tray is structured to receive and hold various deodorizing devices which are in use. Typically these include a bottle with a valve at its tip for maintaining in the tray, i.e., in the bottom member, a measured pool of deodorant or disinfectant liquid, contained in the bottle, a can with a wick in its top, porous impregnated ceramic discs, and porous impregnated fibre wafers. For cooperation with the bottle containing the liquid a wick extends into the liquid deodorant or disinfectant in the pool and is connected through a tube of J configuration to an outlet which carries an outlet tube that typically extends into a commode or urinal. From the wick, the deodorant or disinfectant is dripped into the commode or urinal through the outlet tube at a rate set by the height of the end of the wick by raising or lowering the J-tube. In accordance with the teachings of the prior art, the outlet tube is connected to the outlet through a bulkhead fitting. In accordance with this invention, the inner end of the outlet tube is held securely by a molded compression fit including tapered ribs which project from the inner surface of the outlet.

The liquid absorbed by the wick in the can and in the porous ceramic discs and porous fibre wafers is vaporized by a stream of air from a blower, usually battery driven, which is snap-mounted on the back plate above the tray. The tray has studs for positioning the can and the discs and wafers so that the air from the blower flows freely around these components. The battery-blower units accommodate motors of different physical dimensions.

Another feature of this invention is that the bottle which contains the deodorant that is dripped into the commode or urinal is held by a bar which is snap-locked into the back plate.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which.

DETAILED DESCRIPTION OF EMBODIMENT AND PRACTICE OF METHOD

Figures 1, 2:
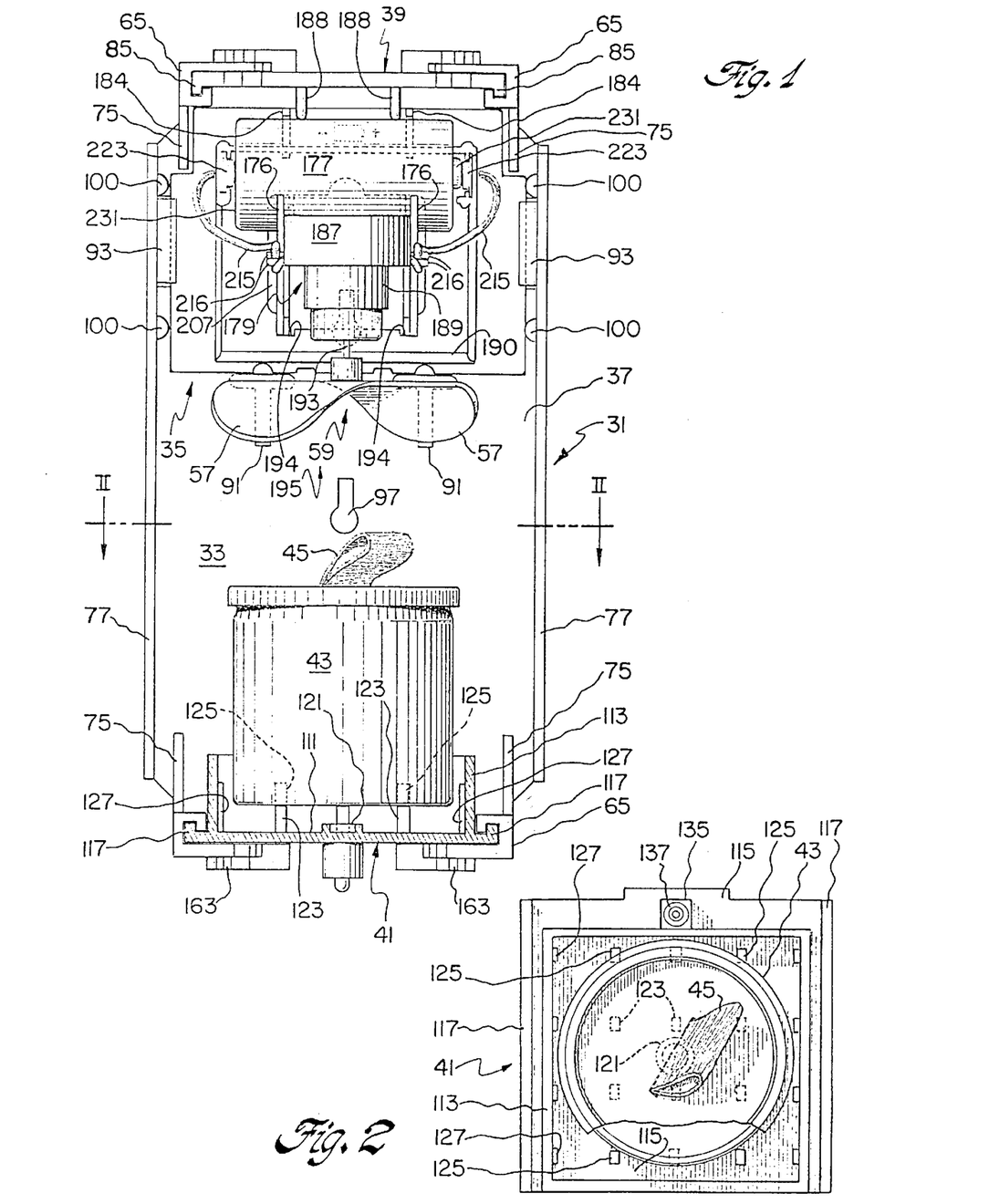
FIG. 1 is a view in front elevation showing apparatus in accordance with this invention made in the practice of the method of this invention.
FIG. 2 is a plan view of the lower member of the apparatus shown in FIG. 1, taken along line II—II of FIG. 1.

The apparatus disclosed in the drawings is an integrated frame assembly 31 for supporting the housing (not shown but shown in Zlotnik) of a cabinet (not shown) for containing facilities for dispensing a deodorant or a disinfectant or the like, particularly in the rest rooms of a public institution. The assembly 31 includes a frame 33 and a battery-blower unit 35 mounted on the frame 33. The frame 33 includes a back plate 37, a top member 39 and a bottom member 41 which is essentially a liquid-tight tray. In FIGS. 1 and 2 a can 43 of a deodorant which has a wick 45 that absorbs the deodorant is shown. The deodorant in the wick is vaporized by a stream of air from the battery-blower unit 35. The can 43 is one of a number of facilities for producing a deodorant or like vapor which the apparatus 31 is adapted to process.

Figure 3:
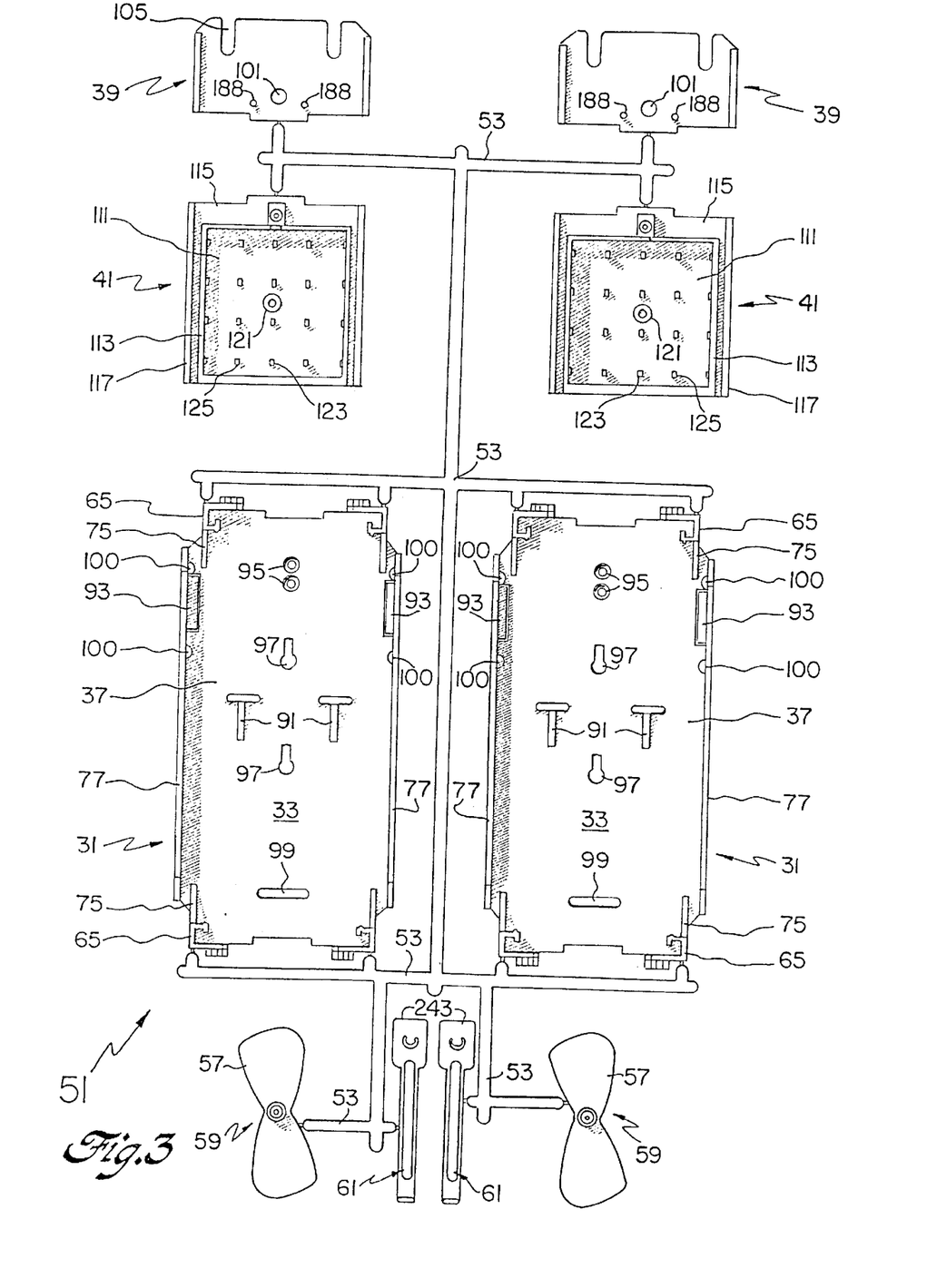
FIG. 3 is a plan view showing the parts of the frame of FIG. 1 and the blades for the blower fan as they appear ready to be removed from the twin molds in which they are formed in the practice of the method of this invention.

The back plate 37, the top member 39 and the bottom member 41 are produced as separate components by molding in the practice of the method of this invention. These components as molded are structured to be joined by snap locks into a rigid frame. FIG. 3 shows a twin mold 51 with the components 37, 39, 41 disposed to be removed by raising them generally parallel to the mold. The twin mold 51 has feed lines 53 for feeding the material into the cavities to form the components. The material is resilient to enable effective joining of the components 37, 39, 41 into a rigid frame by snap locking. Typically, the components are formed of a plastic consisting of 80% polypropylene and 20% fiberglass. In addition to the components 37, 39, 41, blades 57 for the fan 59 (FIG. 12) which drives the air for vaporizing the deodorant and the bottle holders 61 (FIG. 21) are formed in the twin mold 51.

Figure 4:
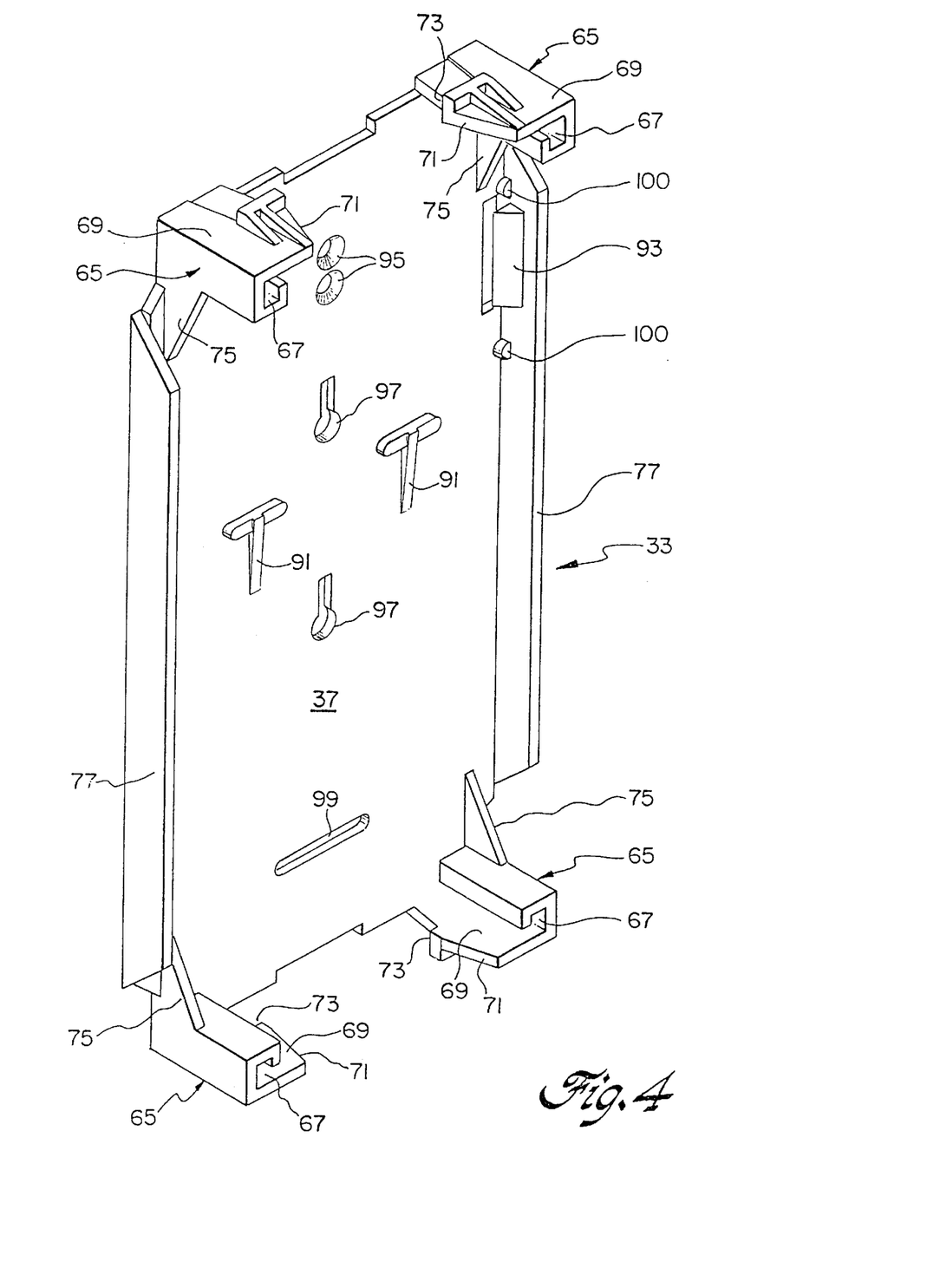
FIG. 4 is a view in isometric showing the back plate of the frame as it is formed in the practice of the method of this invention.

For producing the rigid joints, the back plate 37 is provided with generally perpendicular outward projections 65 FIGS. 1, 3 and 4 at its corners.

Each projection is generally of J transverse cross section, with the long arm 69 of the J extending inwardly, defining a cavity or seat 67 (FIG. 4). Along the end, remote from the cavity, i.e., at its inner end, the long arm 69 of the J section expands into a ramp 71, terminating in a slot 73. A triangular bracket 75 forming part of the back plate 37 proper and of each projection 65 reinforces the connection of the projection to the back plate. Projections 77 extend from the long sides of the back plate 37 to strengthen it. The slots 67 are formed by a core connected to the body of the mold which are removed with the mold when the back plate 37 is removed from the mold. The projections 77 extending from the long sides of the back plate 37 are of small width and the parts of the mold which forms them is readily removed. The slots 67, the projections 77 and other like items present no difficulty in removal from the mold. The mold for the back plate 37 consists of front and back sections which are separated simultaneously when the ned of the molding cycle is complete. When the mold separates, it is a direct pull from either the front side or the rear side of the back plate. therefor requiring no retraction to take place. The top member 39 (FIG. 5) is formed with a locking bar 81, corresponding to each projection. A locking tab 83 extends at an angle from each locking bar 81. Projections 85 extend from the shorter sides of the top member 39.

Figure 5:
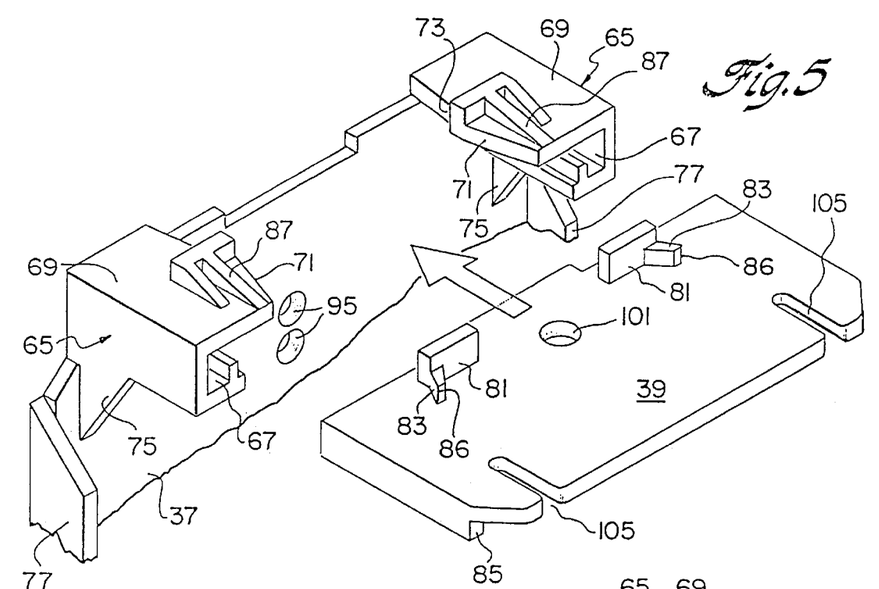
FIG. 5 is an exploded fragmental view in isometric of the upper part of the back plate and the top member showing the relationship of these components in the region where they are joined.
Figure 6A:
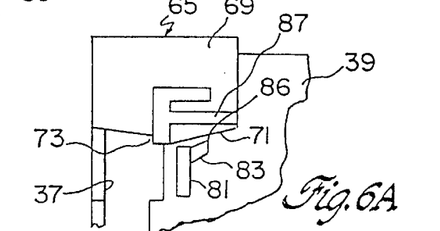
FIGS. 6A, 6B, 6C and 6D are fragmental plan views showing progressively how the top member is snap-locked into the top of the back plate.
Figure 6B:
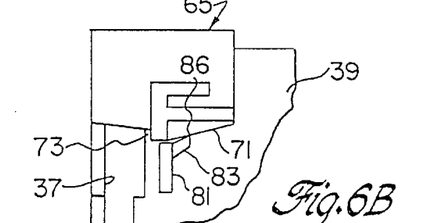
Figure 6C:
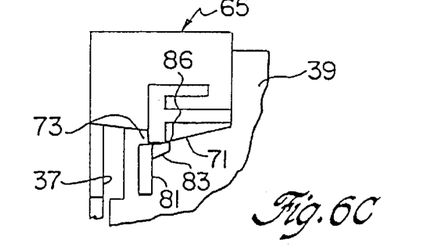
Figure 6D:
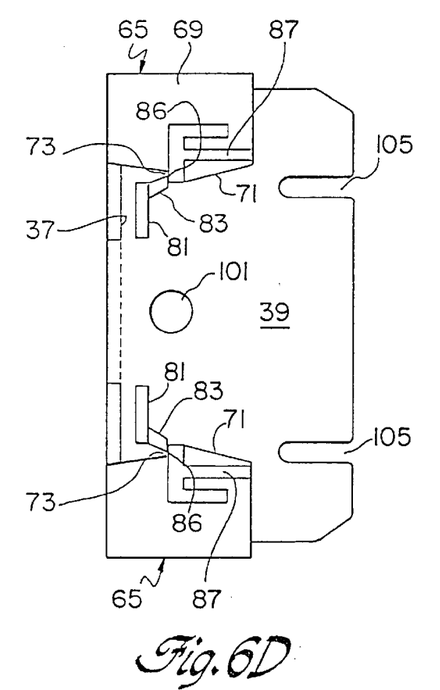
Figure 7:
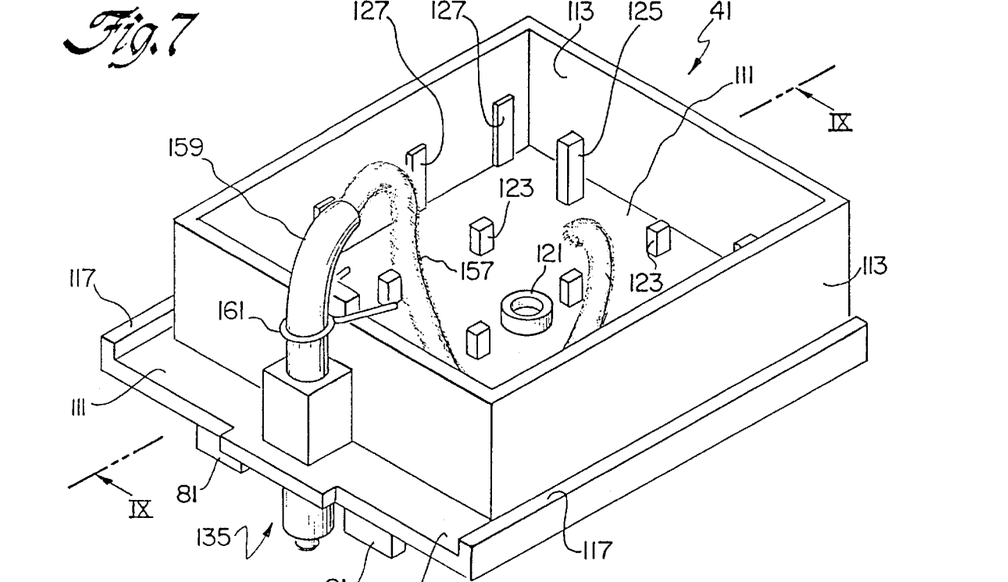
FIG. 7 is a view in isometric showing the bottom member of the frame, i.e., the tray, adapted to drip deodorant or disinfectant from a bottle into a commode or a urinal.

The top member 39 is joined to the back plate 37 in the practice of the method of this invention by engaging the top member 39 with the back plate at the upper end of the back plate and thrusting the upper member into the back plate perpendicularly to the back plate 37 (FIG. 5). The progression of the engagement is shown in FIGS. 6A through 6D. The locking tabs 83 and the projections 85 on the top member 39 are so spaced that tips 86 of tabs 83 are moved inwardly along the ramp 71 and the projections 85 (FIG. 5) move into the slots 67 with the undersides of the long arms 69 of the projections 65 engaging the top of the member 39. The projections 85 are a tight fit in the slots 67 so that the inward thrust of the top plate is resisted, increasing the rigidity of the joint. The locking tabs 83 are compressed (FIGS. 6A–6C). When the top member reaches a position where the tabs 83 are at the end of the ramp 71, the tabs spring into the slots or openings 73 (FIG. 6D) and the tabs 83 relax snap-locking the top member 39 to the back plate 37. The projections 85 extend into the slot 67 strengthening the lock. The top member 39 and the back plate can be dimensioned of substantial thickness so that the joint is more rigid than the molded joint in Zlotnik.

The locking bars 81 cooperate with the ramps 87 (FIG. 5) at the top of the back plate to lock the housing (not shown) by engagement with the lock tabs 10 (FIGS. 3, 4 Zlotnik) as disclosed in Zlotnik.

In addition to the structures described above, the back plate 37 has ramps 91 and runners 93 for securing the battery-blower unit and openings 95, 97, 99 for mounting the frame 31 on a wall (FIG. 4). On the internal surface of the projections 77, there are spacers 100 (FIGS. 4 and 13) for aligning the battery-blower unit 35. The top member 39 has holes 101 (FIGS. 3 and 5) for attachment of the bottle holder 61 and slots 105 for a motor (not shown) in the event that external power supplies the cabinet for driving the motor of the blower.

The bottom member 41 is a liquid-tight tray (FIGS. 7–11). The base 111 of the tray extends beyond its vertical walls 113 on one side, providing a shelf-like surface 115 on one side. Projections 117 extend along opposite ends of the base of the tray.

In the center of the tray there is a ring 121. A plurality of studs 123, 125 and 127 arrayed in rows generally perpendicular to each other project upwardly from the base 111. The studs 123 are short, the studs 125 which are near the corners of the array are longer and the studs 127 which project integrally from the wall 113 are of the same length as the studs 125.

Figure 13:
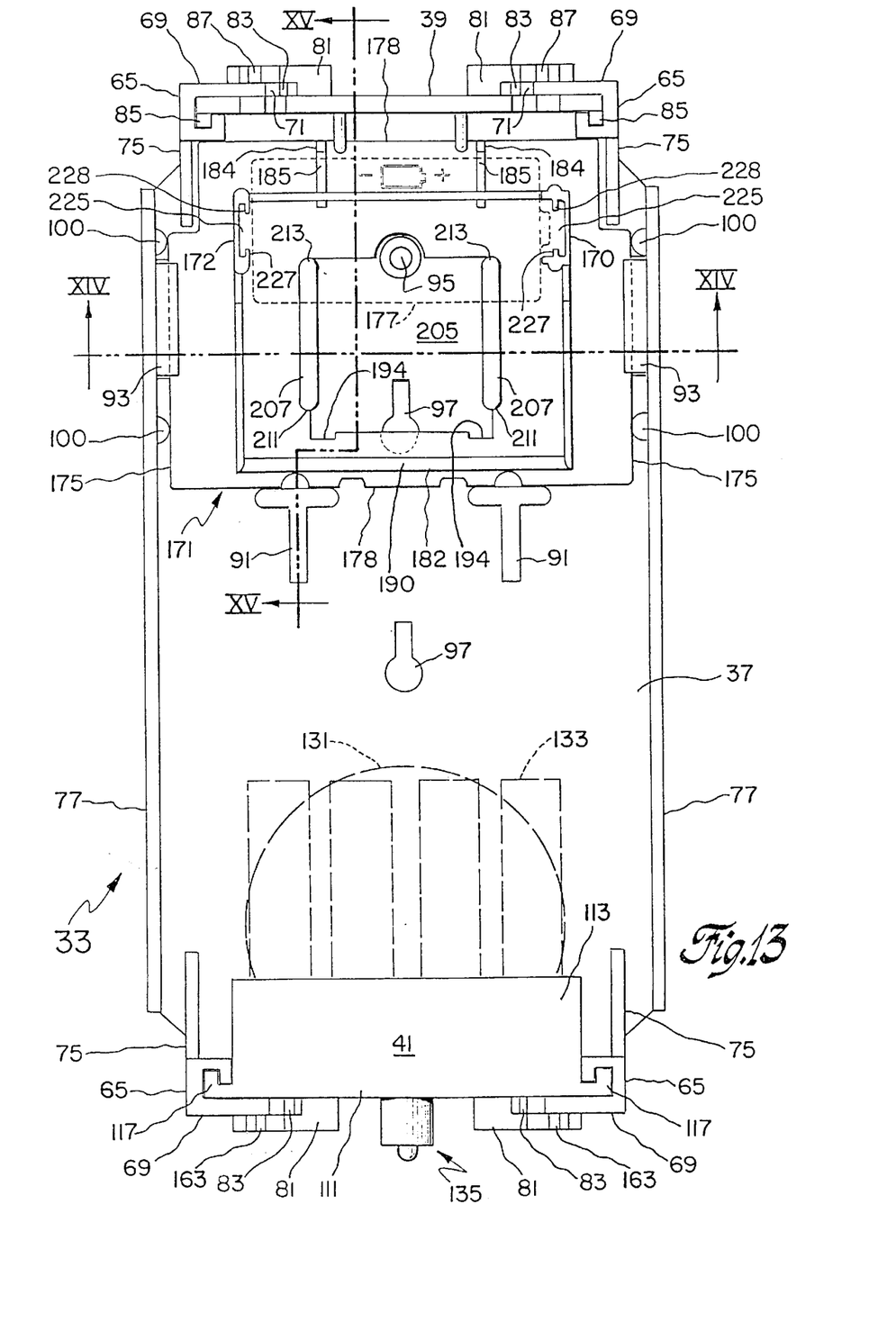
FIG. 13 is a view in front elevation of the frame showing the facilities for mounting the battery-blower unit.

FIG. 1 shows the can 43 supported on the short studs 123 and spaced from the walls 113 by being nested in the upward projecting studs 125 in the corners (FIGS. 1, 2). The can 43 is thus prevented from moving. The air which vaporizes the liquid in the wick thus has space for unobstructed flow. As shown in FIG. 13, the ceramic discs 131 are mounted in one orientation and the wafers 133 are mounted in an orientation at right angles to the surcotas. The ceramic discs 131 and wafers 133 are spaced by the studs so that air circulates from the battery-blower unit 35 contacts these components on all sides to diffuse the deodorant vapors. Studs 123 in a rectangular array, and studs 125 and 127 are provided to position and hold erect the wafers 133, typically four in number, aligned and ceramic discs 131, typically three in number, aligned generally at right angles to the wafers.

Figures 8, 9, 10, 11:
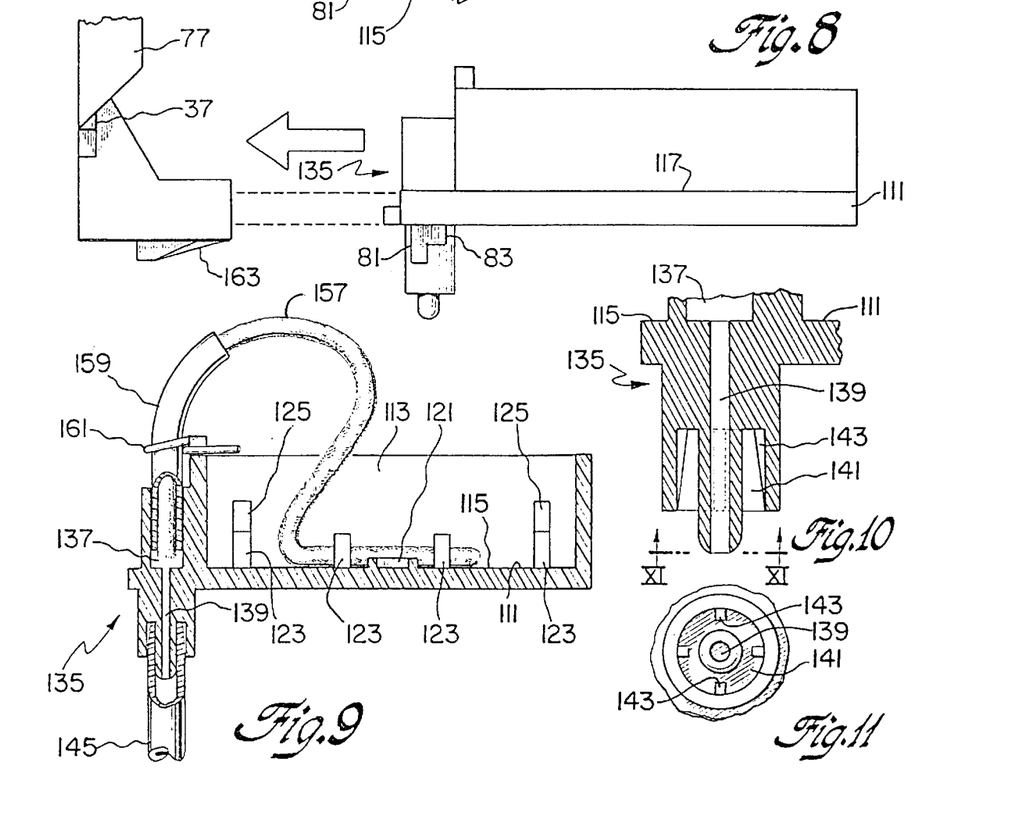
FIG. 8 is a view in side elevation showing how the bottom member of the frame is joined to the back plate.
FIG. 9 is a view in transverse section taken along line IX—IX of FIG. 7, but with the wick and J-tube of the drop assembly not sectioned.
FIG. 10 is an enlarged fragmental view in longitudinal section showing the projection which accommodates the tubes through which the deodorant or disinfectant is dripped into a commode or urinal.
FIG. 11 is a view in end elevation taken in the direction XI—XI of FIG. 10.

A projection 135 (FIGS. 9, 10, 11) extends integrally from the shelf 115. The projection includes an upper channel 137 in communication with a constricted channel 139. Extending into the end of the projection, there is an annular opening 141. From the inner periphery of the opening ribs 143 extend axially (FIG. 10). The ribs 143 are tapered radially expanding inwardly. A drip tube 145 extends into the opening 141 and is held firmly by the tapered ribs 143. Bulkhead fittings are thus dispensed with.

Figure 18:
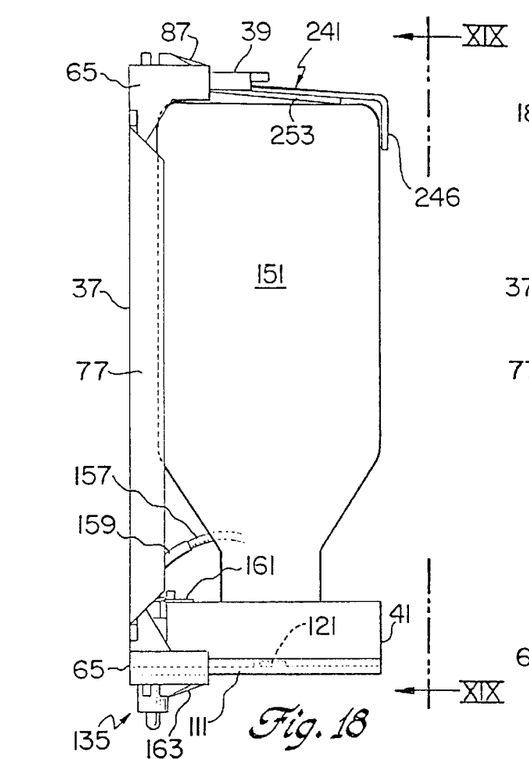
FIG. 18 is a view in side elevation showing the mounting for the bottle from which the deodorant or disinfectant is dripped.
Figure 19:
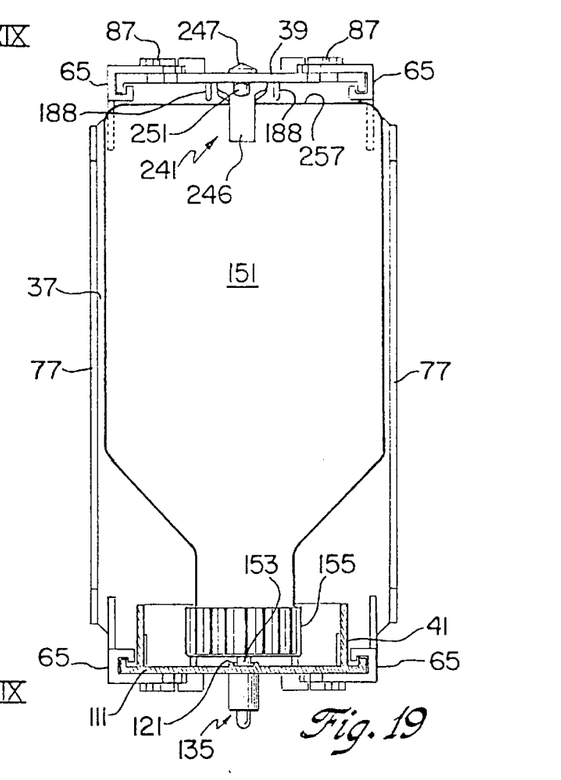
FIG. 19 is a view in side elevation and partly in section taken in the direction XIX—XIX of FIG. 18.

The projection 135 serves when the apparatus according to this invention is used to drip drops of a deodorant or the like from a bottle 151 (FIGS. 18, 19) into a commode or urinal (not shown). The bottle 151 has a valve 153 in its cap 155. As shown in FIG. 19, the bottle 151 is centered on the ring 121 in the tray 41. The valve 153 is opened depositing the deodorant in the tray to a level at which penetration of air in the bottle is precluded. A wick 157 (FIGS. 7, 9) is disposed in the liquid in the tray 41 with its opposite end extending through a J-tube 159 into the opening 137. Drops from the wick 157 drip into the tube 145 and perform the deodorant function. The wick 157 is adjustable vertically by raising or lowering the J-tube 159 to set the rate at which the drops are deposited into the commode or urinal through the tube 145. The adjustment is effected by moving the J-tube 159 upwardly or downwardly. The J-tube 159 and the wick 157 may be locked in any position by clamp 161.

The bottom member 41 is secured to the back plate in the same way as the top member 39. On its underside, the base 111 has integrally locking bars 81 from which locking tabs 83 extend. When the member 41 is thrust into the back plate 37, the locking tabs are compressed by ramps 163 (FIG. 8) and when they leave the ramps, they relax and snap lock the member 41 to the back plate. The joint is strengthened by the engagement of the projections 117 in slots 67 in the projections 65 at the bottom of the back plate 37 (FIG. 4). The projections 117 are a tight-fit in the slots 67 resisting the thrust exerted on the top plate and thus contributing to achieve a rigid structure.

The back plate 37 has at the bottom ramps 87 and with the locking bars 81 on the underside of the bottom member 41 cooperate with lock tabs (10, FIG. 3 Zlotnik) at the bottom of Zlotnik's housing as disclosed in Zlotnik to lock the housing on the frame 33.

Figures 12, 14, 15, 16:
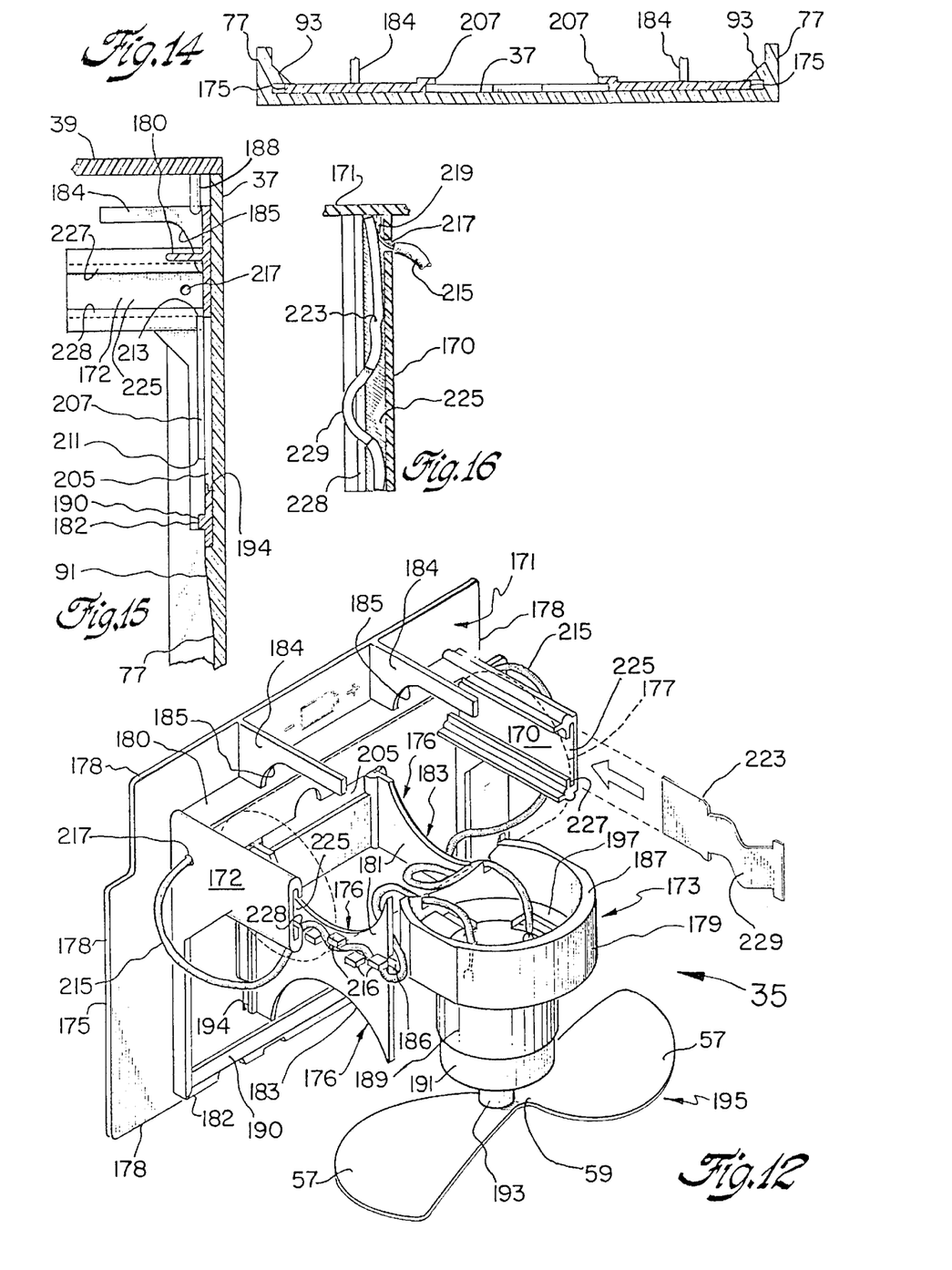
FIG. 12 is a view in isometric showing the complete battery-blower unit in accordance with this invention which is integrated into the back plate of the frame.
FIG. 14 is a view in transverse section taken along line XIV—XIV of FIG. 13.
FIG. 15 is a view in partial longitudinal section taken along line XV—XV of FIG. 13.
FIG. 16 is a fragmental view partly in section showing the connection of a motor terminal wire at its point of contact to the battery with a metal clip and without soldering.

The battery-blower unit 35 (FIG. 12) includes the supporting plate 171 and the battery motor bracket 173. The supporting plate 171 is rigidly mounted on the back plate 37. The outer sides 175 of the supporting plate 171 are thrust upwardly through the runners 93, while the inner surface of the plate at the bottom rides on the ramps 91 (FIG. 13). This inner surface is flexed and is under stress when insertion takes place. When the inner surface of the plate 171 springs from the ramps 91, the plate 171 is snap-locked to the back plate 37. The runners 93 and the plate 171 at its ends are a tight fit so that the passage of the ends of the plate through the runners is resisted and the plate 171 is flexed. Once plate 171 is fully positioned in the runners, it relaxes producing a snap-lock. The plate 171 is also held by pins 188 which extend from top member 39 (FIGS. 1, 3, 15). The plate 171 is aligned by the spacers 100 in the projections 77 of back plate 37. Near the top, channels 170 and 172 extend from opposite ends of support plate 171 spaced a short distance outwardly from positive pole 231 (FIG. 1) and the negative pole (not shown) respectively. The flanges 227 of channel 170 are spaced further apart than the flanges 228 of channel 172 to permit the necessary close spacing of channel 170 and the protruding positive pole 231. This structure also precludes improper positioning of the battery. If an attempt were made to position the battery with the positive pole opposite channel 170, there would be no contact with negative battery terminal, necessitating correct polarization for operation of the battery-blower unit 35.

The battery-blower bracket 173 includes a cradle 176 for the battery 177. A motor socket unit 179 extends from the cradle 176. The cradle 176 includes plates 181 whose opposite vertical surfaces 183 are arcuate to provide seats for the battery 177. The arcuate seats 183 for the battery 177 in opposite surfaces constitute a cradle for the battery in each of opposite mountings of the battery-blower bracket 173. To hold the battery 177 securely, the supporting plate 171 is provided with holding bars 184 which have curved edges 185 to match the contour of the battery. The holding bars 184 are seated in the right angle joint formed between the outer perimeter 178 of the supporting plate 171 and projecting shelf 180 part of a frame-like structure 182 internally of plate 171. The motor socket unit 179 is supported by projections 186 connected to the outer ends of the plates 181. The motor-socket unit 179 includes a socket 187 for a motor of larger dimensions and a socket 189 for a motor 191 of smaller dimensions. In FIG. 12 a motor 191 is shown in its socket 189. The drive shaft 193 of the motor is connected to drive fan 195 having blades 57. The sockets 187 and 189 are connected back-to-back so that each can be above or below as bracket 173 is oriented. The socket 187 includes an internal annular surface 197 (FIG. 17) which may be arcuate for supporting the motor of larger dimensions. The motor 191 of smaller dimensions is supported in a ring 201 under or above the surface 197 depending on how the bracket 173 is oriented. The motor of larger dimensions is held in the socket 187 by friction and the motor 191 of smaller dimensions is held in the ring 201 by a lip 202 along the outer edge of socket 189 (FIG. 17A).

The supporting plate 171 has a generally central opening 205 having a generally rectangular boundary. Along opposite vertical sides of the boundary there are tracks 207 (FIG. 13). The tracks 207 extend only partly along the opposite sides (FIG. 17). At the end of the battery-motor bracket 173, remote from the socket unit 179, the bracket has opposite slots 209 dimensioned and spaced to engage the tracks 207. To mount the battery-blower bracket 173 on the supporting plate 171, the slots 209 are engaged with the track 207 at the points 211 where the tracks terminate, i.e., at the bottom when the supporting plate is mounted on the back plate 37, and are moved along the track (FIG. 13). When the slots 209 reach the ends 213 of the tracks 207, they are stopped by the body of the supporting plate 171. The slots 209 are a tight fit on the track 207 and they are stressed while being moved. When the movement is stopped, the slots are relaxed and the bracket 173 is snap-locked on the support plate 171. In addition, the slotted members 209 are forced over the lower bar 190 of the frame 182 and when they clear the inner end of the bar 190 spring into snap lock state. The forced movement of the bracket continues and the ends of the slot 209 spring over edge 194 producing an additional snap lock. The slots 209 are interchangeable with the tracks 207 so that the bracket 173 can be mounted with the socket 189 below the socket 187 or the socket 189 may be mounted above and the socket 187 below.

The channels 170 and 172 extending from support plate 171 serve to connect the leads or wires 215 from motor 191 or a motor in the socket 187 to the battery 177. The wires 215 are guided by nubbins 216 on the plates 181 of battery cradle 176 (FIGS. 12, 17). Each channel 170 and 172 has a hole 217 in its inner end (FIG. 15). The stripped end 219 of each wire 215 from the motor terminals (not shown) is passed through this hole (FIG. 16) and extends inwardly of the channels 170 and 172. A metal strip 223 is inserted in the slots 225, formed by the flanges 227 and 228 of the channels. Each strip 223 firmly engages the stripped end 219 of a wire 215 and it has a bulge 229 which engages the adjacent pole 231 of the battery. Each wire is thus connected to a pole of the battery.

Figures 17, 17A:
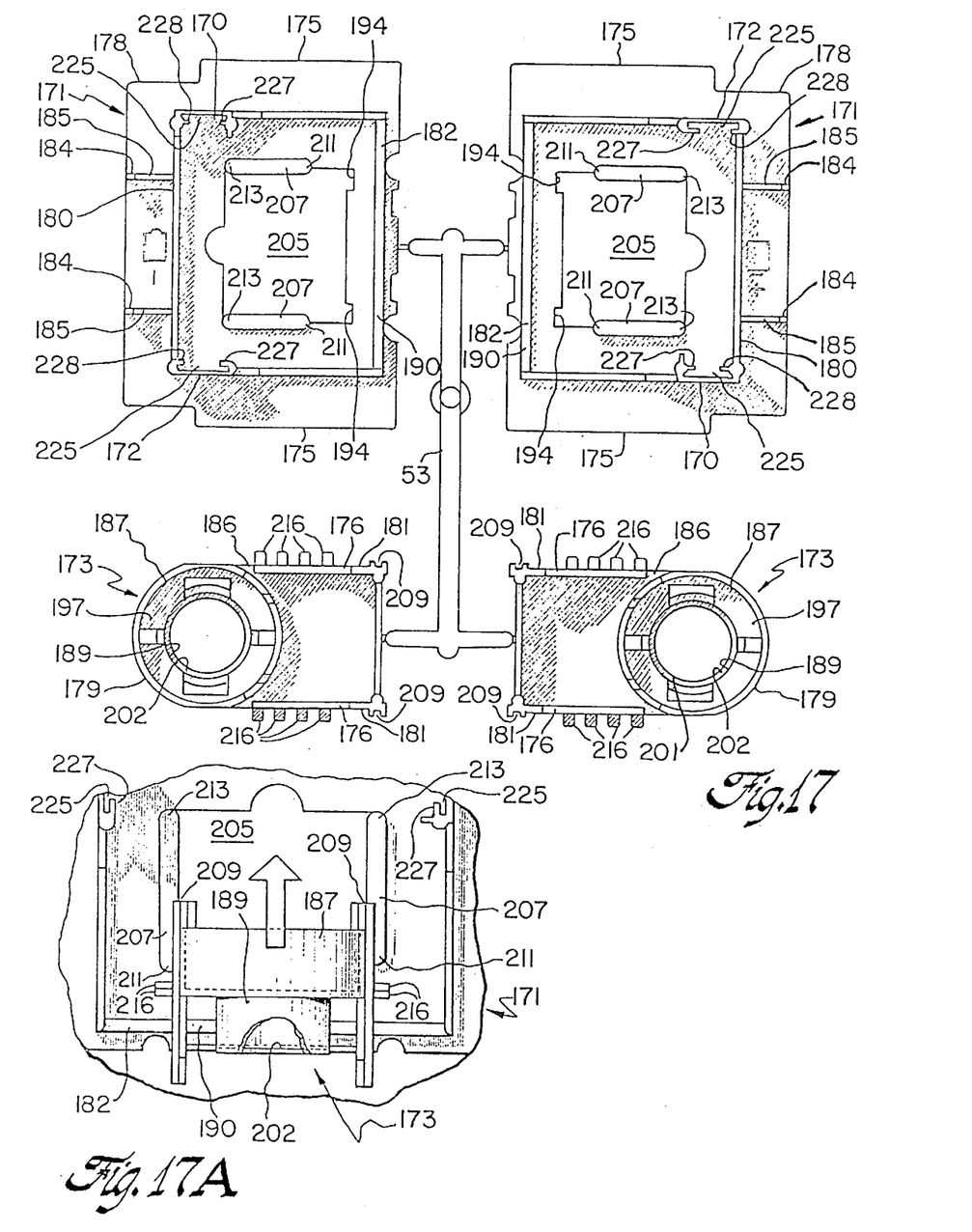
FIG. 17 is a plan view showing the blower assembly as it is completed and removable from twin molds.
FIG. 17A is a fragmental view in elevation showing how the battery-blower unit is mounted on the support plate.

As shown in FIG. 17, the supporting plate 171 and the battery-motor unit 173 are formed in twin molds. The components 171 and 173 are formed typically of a material such as acrylic butylene and styrene. This material serves to produce a structure of greater strength than the polypropylene fiberglass typical of the material from which the other components such as the back plate 37, the top member 39 and the bottom member 41 are formed. The additional strength is necessary because the components 171 and 173 are subjected to higher stresses by the moving parts which they support. The components 171 and 173 are positioned in the mold so that they can be readily removed and snapped together to produce a sturdy motor-battery holder assembly.

Figure 20:
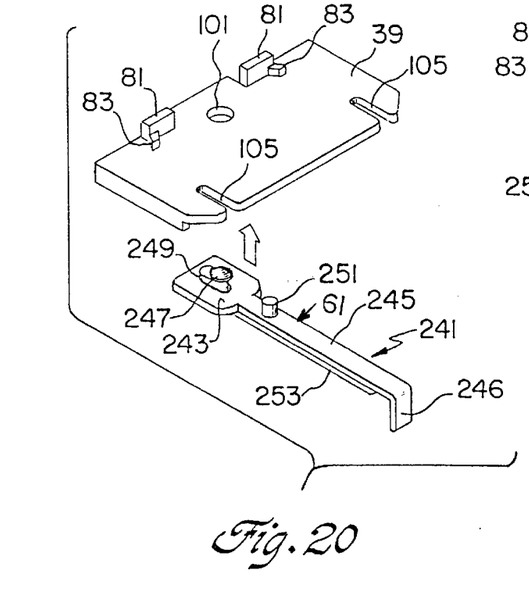
FIG. 20 is an exploded view in isometric showing the relationship between the bottle holder and the top member.
Figure 21:
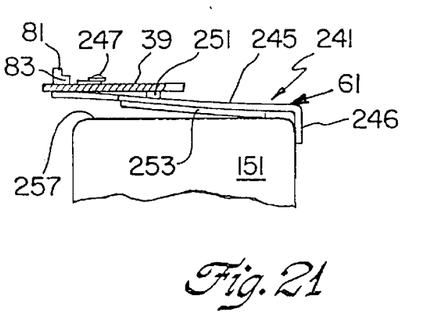
FIG. 21 is a fragmental view in side elevation showing the manner in which the bottle holder engages the bottle.

The bottle holder 61 (FIGS. 20, 21) includes an L-shaped bar 241 having a generally rectangular section 243 at the end, joined to a narrower strip 245 by rounded sides (FIGS. 20, 21). At its opposite end, the strip 245 is bent generally at right angles forming the end 246 of the L. Generally, centrally of the section 243, there is a stud 247 partly encircled by a J-shaped strip 249.

A second stud 251 extends from the strip 245 a short distance from the rectangular section 243. A second strip 253 of the same width as the strip 245 is secured to the first strip 245 near its joint with the section 243 and extends cantilever like under the strip 245 part way to L-tip 246.

The bottle holder 61 is mounted under top member 39 by engaging stud 247 and J-strip 249 in opening 101 in top member 39. The stud 247 is compressed on being inserted in opening 101 and when it relaxes and expands, it snap-locks the bottle holder 61 to the top member 39. The top member 39 exerts a compressive force on second stud 251, pressing the strip 253 against the top 257 of the bottle 151 holding the bottle firmly (FIG. 20).

While preferred embodiments of this invention have been disclosed herein, many modifications thereof are feasible. This invention is not to be restricted except insofar as is necessitated by the spirit of the prior art.

What is claimed is:

1. For a cabinet having a housing for facilities for supplying a deodorant, a frame for receiving the housing; said frame being of generally C longitudinal cross-section and including: a back plate, a top member and a bottom member each separately constructed and composed of a flexible material; projections extending generally perpendicularly outwardly from corners at a top and bottom of said backing plate, said top member and bottom member having a substantial thickness for opposite lateral sides thereof to engage and form rigid joints between the respective ones of said projections at the top and bottom of the back plate; and cooperative flexible interlocks formed on said back plate, said top member and said bottom member for joining the top member and bottom member rigidly to said back plate transversely with reference to said back plate.

2. For a cabinet having a housing for facilities for supplying a deodorant, a frame for receiving the housing; said frame being of generally C longitudinal cross-section and including: a back plate, a top member and a bottom member, said back plate, top member and bottom member each being separately constructed, said back plate and members being composed of a flexible material, cooperative flexible interlocking means formed on said back plate and on said top member for joining said top member rigidly to said back plate transversely with reference to said back plate, and cooperative flexible interlocking means formed on said back plate and on said bottom member for joining said bottom member rigidly to said back plate transversely to said back plate, said back plate, and said members being of substantial thickness thereby to form a rigid frame of substantial thickness providing rigid joints characterized by that the cooperative interlocking means for joining the top member to the back plate includes ramp means formed on a surface of said back plate and locking tab means formed on a surface of the top member, said tab means being adapted to be moved into engagement with a surface of said ramp means by the movement of said top member generally transversely to said back plate until said tab means, having been compressed by said movement, disengages said ramp means as said tab means moves in engagement therewith and on the disengagement of said tab means from said ramp means to relax from the compression and snap into locking engagement with said back plate.

3. The frame of claim 2 wherein the surface of the ramp means engaged by the tab means is generally transverse to the surface of the back plate.

4. The frame of claim 2 characterized by that the locking tab means is disposed on the upper surface of the top member.

5. The frame of claim 2 wherein the back plate includes projection means having the ramp means connected thereto and the projection means also includes means to be connected to a housing to form the cabinet.

6. The frame of claim 5 wherein the ramp means has a surface on the projection means engagable by the tab means, said surface being generally transverse to the surface of the back plate from which the projection means extend, and the means to be connected to the housing includes slots in the projection means generally parallel to the surface of the back plate.

7. The frame of claim 5 wherein the top and bottom members include locking bar means cooperative with the means to be connected to the housing to effectuate the mounting of the housing on the frame.

8. The frame of claim 2 wherein the cooperative interlocking means includes member projections on each of the top member and bottom member along their edges positioned generally perpendicularly to the back plate and the back plate includes back plate means having slots engaged by said projections when the top and bottom members are moved towards the back plate in the compression of the locking tab means.

9. The frame of claim 2 wherein slot means having a slot is associated with the ramp means and the top member has a projection, said projection being adapted to engage the slot of said slot means as the locking tab means is moved into engagement with the surface of the ramp means.

10. For a cabinet having a housing for facilities for supplying a deodorant, a frame for receiving the housing; said frame being of generally C longitudinal cross-section and including: a back plate, a top member and a bottom member, said back plate, top member and bottom member each being separately constructed, said back plate and members being composed of a flexible material, cooperative flexible interlocking means formed on said back plate and on said top member for joining said top member rigidly to said back plate transversely with reference to said back plate, and cooperative flexible interlocking means formed on said back plate and on said bottom member for joining said bottom member rigidly to said back plate transversely to said back plate, said back plate, and said members being of substantial thickness thereby to form a rigid frame of substantial thickness providing rigid joints characterized by that the cooperative interlocking means for joining the bottom member to the back plate includes ramp means formed on a surface of the back plate and locking tab means formed on a surface of said bottom member; said tab means being adapted to be moved in engagement with a surface of said ramp means by movement of said bottom member generally transversely to said back plate until said tab means disengages said ramp means, said tab means to be compressed by said ramp means as said tab means moves in engagement therewith and on the disengagement of said tab means from said ramp means to relax from the compression and snap into locking engagement with said back plate.

11. The frame of claim 10 wherein the surface of the ramp means engaged by the tab means is generally transverse to the surface of the back plate.

12. The frame of claim 10 characterized by that the locking tab means is disposed on the bottom surface of the bottom member.

13. A method of making a frame, of generally C longitudinal cross-section and of substantial thickness providing rigid joints, for receiving the housing of a cabinet for facilities for supplying a deodorant, said facility including a blower for producing a stream of air for vaporizing a deodorant having a fan with a blade, said method comprising: molding of a flexible material as separate components, a back plate, a top member and a bottom member, said plate and members being of substantial thickness; said back plate having molded near the top of one surface thereof and said top member having molded on a corresponding one surface thereof first flexible cooperative means for joining said back plate and top member into a rigid assembly, said back plate having molded near the bottom of said one surface thereof and said bottom member having molded on a corresponding one surface thereof, second flexible cooperative means for joining said back plate, and bottom member into a rigid assembly; and with said first and second cooperative means respectively joining said back plate, said top member and said bottom member into a rigid frame, said method being characterized by that the blade, the back plate, the top member and the bottom member are produced in a unitary mold assembly.

14. A method of making a frame, of generally C longitudinal cross-section and of substantial thickness providing rigid joints, for receiving the housing of a cabinet for facilities for supplying a deodorant, comprising: molding of a flexible material as separate components, a back plate, a top member and a bottom member, said plate and members being of substantial thickness; said back plate having molded near the top of one surface thereof and said top member having molded on a corresponding one surface thereof first flexible cooperative means for joining said back plate and top member into a rigid assembly, said back plate having molded near the bottom of said one surface thereof and said bottom member having molded on a corresponding one surface thereof, second flexible cooperative means for joining said back plate, and bottom member into a rigid assembly; and with said first and second cooperative means respectively joining said back plate, said top member and said bottom member into a rigid frame, the flexible cooperative means for joining the back plate and top and bottom members including ends on the back plate first ramps and second ramps respectively near the top and bottom thereof and also including on the top member first locking tabs near the end thereof and on the bottom member second locking tab near an end thereof; the said method being characterized by compressing said first locking tabs by moving said top member towards said back plate with the first tabs moving along said first ramps in engagement with said first ramps, relaxing the compression of said first tabs by continuing the movement of said top member towards said back plate until the first tabs are disengaged from said first ramps, thereby to snap the first locking tabs into firm engagement with said first ramps and snap said top member and said back plate into rigid engagement; and the said method being further characterized by compressing said second locking tabs by moving said bottom member towards said back plate with said second tabs moving along said second ramps in engagement with said second ramps, relaxing the compression of said second tabs by continuing the movement of said bottom member towards said back plate until said second tabs are disengaged from said second raps to snap the second locking tabs into firm engagement with said second ramp, and snap said bottom member and said back plate into rigid engagement.

* * * * *